(12) United States Patent
Otto et al.

(10) Patent No.: US 6,290,727 B1
(45) Date of Patent: Sep. 18, 2001

(54) ACETABULAR CUP

(75) Inventors: Karl Bernahrd Otto, Ellerbek; Arnold Keller, Kayhude, both of (DE)

(73) Assignees: GMT Gesellschaft für madizinische Technik mbH; Waldemar Link GmbH & Co. KG, both of Hamburg (DE)

( * ) Notice: Subject to any disclaimer, the term of this patent is extended or adjusted under 35 U.S.C. 154(b) by 0 days.

(21) Appl. No.: 09/400,580

(22) Filed: Sep. 22, 1999

(30) Foreign Application Priority Data

Sep. 24, 1998 (DE) ................................................ 198 43 797

(51) Int. Cl.7 .............................................................. A61F 2/32
(52) U.S. Cl. ...................................... 623/22.21; 623/22.39
(58) Field of Search ............................. 623/22.21, 22.23, 623/22.32, 22.38, 22.39

(56) References Cited

U.S. PATENT DOCUMENTS

| | | |
|---|---|---|
| 4,123,806 | 11/1978 | Amstutz et al. . |
| 4,883,490 | 11/1989 | Oh . |
| 5,549,701 | * 8/1996 | Mikhail ............................... 623/22.21 |
| 5,938,702 | * 8/1999 | Lopez et al. ........................ 623/22.24 |
| 6,042,611 | * 3/2000 | Noiles ................................. 623/22.21 |

* cited by examiner

*Primary Examiner*—David J Isabella
(74) *Attorney, Agent, or Firm*—Henry M. Feiereisen

(57) ABSTRACT

An acetabular cup is supported by a pelvic bone and includes an outer surface which rests in a cavity, and a bearing surface which receives an articular body of an artificial hip joint and bounded in surrounding relation by a receiving edge. The receiving edge is provided at least at one area with an elevation which partially surrounds the articular head received by the bearing surface. The elevation is provided at a location in which the articular head is least obstructed in its freedom of movement, and has at its apex projecting furthest from the receiving edge a distance from a lowest point of the bearing surface which guides the articular head in substantially surrounding relation.

32 Claims, 3 Drawing Sheets

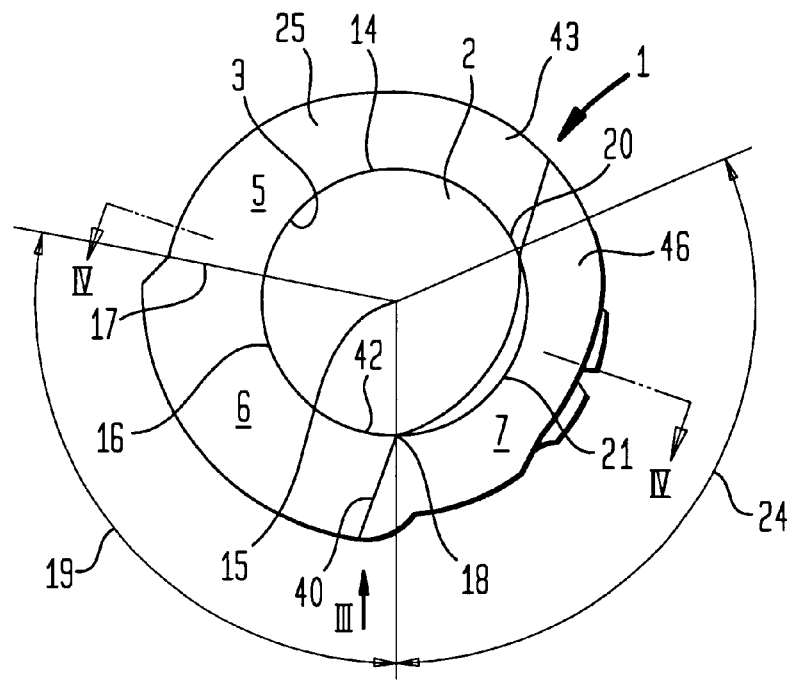
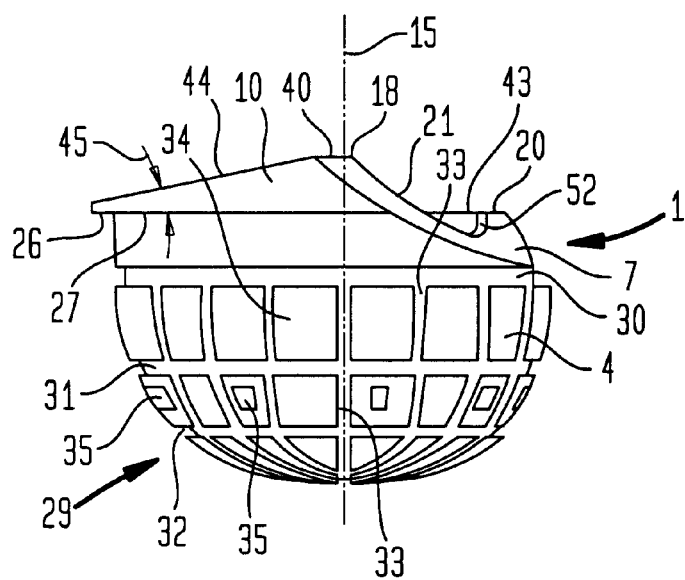

ACETABULAR CUP

BACKGROUND OF THE INVENTION

The invention relates to an acetabular cup which is supported by a pelvic bone and includes an outer surface resting in a cavity, and a bearing surface receiving an articular body of an artificial hip joint and bounded in surrounding relation by a receiving edge.

An acetabular cup of this type is known, for example, from U.S. Pat. Nos. 4,883,490 and 4,123,806. These conventional acetabular cups suffer shortcomings when implanted in a leg or femur because undesired luxations have been experienced during certain movements. In order to reduce the risk of dislocation of the articular head from the acetabular cup, the depth of the spherical segment in the acetabular cup could be increased. This, however, would be accompanied at the same time by a restriction of movement and a resultant undesired functional limitation of the acetabular cup or of the entire hip joint endoprosthesis.

SUMMARY OF THE INVENTION

It is thus an object of the present invention, to so improve the conventional acetabular cups that the risk of an undesired luxation is reduced, on the one hand, and to substantially eliminate an undesired restriction of movement.

This object is attained in accordance with the present invention by providing the receiving edge at least at one area with an elevation which partially surrounds the articular head received by the bearing surface.

By providing the receiving edge with an elevation, it is possible to create in this region the acetabular cup with a depth which is greater than the radius of the spherical section, so that an inserted articular head is form-fittingly enclosed by the bearing surface of the acetabular cup and snaps into the acetabular cup. In the imperiled movement range, an intended blocking is thus realized that prevents a luxation. The region that is not affected by the elevation does not experience an unnecessary blocking or undesired restriction of movement.

According to a preferred embodiment of the invention, the elevation is provided in an area of least obstruction to the freedom of movement of the articular head. In this way, luxations are greatly diminished, on the one hand, and, on the other hand, the freedom of movement of the articular head is impeded only in those zones in which only very rare movement patterns occur.

According to a further preferred embodiment of the invention, the elevation has at its apex, projecting furthest from the receiving edge, a distance from a lowest point of the bearing surface which guides the articular head in a substantially surrounding relation. In this way, the articular head can snap into the bearing surface, so as to be able to execute within the bearing surface movements which are merely impaired by the elevation, but otherwise allows the relevant part of the freedom of movement desired for a femur.

According to a further preferred embodiment of the invention, the elevation extends from the lowest point of the bearing surface to the apex in a direction in which a femur which receives the artificial hip joint extends slantingly backwards with respect to a stretched standing leg and thereby intersects at an acute angle an imaginary movement plane which is defined by the standing leg in straight alignment. Such a movement direction is uncommon for a femur and is rarely executed. An impairment with respect to this movement direction is thus barely noticeable for a bearer of a hip joint and thus hardly interfering. Still, the elevation has the crucial advantage of substantially preventing luxations of the hip joint.

According to a further preferred embodiment of the invention, the bearing surface is designed as a spherical section of an inner surface which is circumscribed by a hollow sphere and which is formed by a part of a sliding surface of the elevation, confronting the articular head which is configured as spherical head. This sliding surface formed at the elevation fits in the bearing surface formed as hollow sphere, so as to enable optimum guiding conditions for an articular head configured as spherical head.

According to a further preferred embodiment of the invention, the receiving edge is formed in a first segment as edge region of a spherical section extending substantially in a horizontal plane and defining a plane upon which a cup axis is oriented perpendicular and extending through the lowest point. Following a first segment of the receiving edge is a second segment which includes the elevation and ascends from a junction end, adjacent the first segment, of the second segment to the apex of the elevation. The rise of the elevation in the second segment enables an optimization between luxation risk, on the one hand, and freedom of movement, on the other hand.

According to a further preferred embodiment of the invention, the first segment has a first end distal to the junction end of the second segment, wherein between the first end of the first segment and the apex of the elevation of the second segment there is arranged a third segment in which the receiving edge is depressed in the direction to the lowest point for clearing a pivot space within which a stem, secured to the femur, of the spherical head is swingably supported. This pivot space realizes that the stem, connected to the articular head, is not interfere with by the receiving edge when carrying out swivel motions. The guidance of the articular head is diminished in the area of the pivot space and is sufficiently compensated by the elevation. Therefore, the pivot space drops immediately in the direction toward the first end of the apex. Moreover, the receiving edge in the area of the pivot space is slanted in a plane which extends at an acute angle to a plane oriented perpendicular to the cup axis. This plane defined by the pivot space is so configured as to allow in this area an unimpeded movement of the stem secured to the articular head.

According to a further preferred embodiment of the invention, the receiving edge has in the pivot space with respect to the lowest point a height for guiding the spherical head in a form-fitting manner, and a cut-off edge which permits the insertion of the spherical head in the bearing surface. In this manner, the receiving edge can be moved up in the area of the pivot space to a relatively high location at the articular head, without complicating the insertion of the articular head which is inserted via the cut-off edge into the bearing surface.

According to a preferred embodiment of the invention, the receiving edge is formed in a first segment as edge of a spherical section which substantially extends transversely to a cup axis. The first segment of the receiving edge terminates in a second segment which includes the elevation and which ascends from a junction end, adjacent the first segment, of the second segment to an apex of the elevation. The rise of the elevation in the second segment realizes an optimum between luxation risk and freedom of movement.

According to a further preferred embodiment of the invention, the first segment has a first end distal to the junction end of the second segment, wherein between the first end of the first segment and the apex of the elevation of the second segment there is arranged a third segment which forms the edge of a spherical section arranged at an acute angle to the cup axis so as to generate in this area a depth which is less than the depth of the first segment and smaller than the radius of the spherical section. The spherical section in the less imperiled third segment realizes an increased freedom of movement as a consequence of the reduced depth, without increasing the luxation risk compared to the known state of the art.

According to a further preferred embodiment of the invention, the outer surface has a plurality of spacers in substantial concentric relation to the cup axis. When cementing the acetabular cup, the spacers effect a more even layer thickness of the bone cement being used.

Further specifics of the invention will now be described in more detail with reference to the attached drawing in which preferred embodiments of the invention are illustrated by way of example, and in which:

BRIEF DESCRIPTION OF THE DRAWING

FIG. 2 is a top view of an acetabular cup;

FIG. 3 is a side view of the acetabular cup of FIG. 2 in direction III;

DETAILED DESCRIPTION OF PREFERRED EMBODIMENTS

Figure 1:
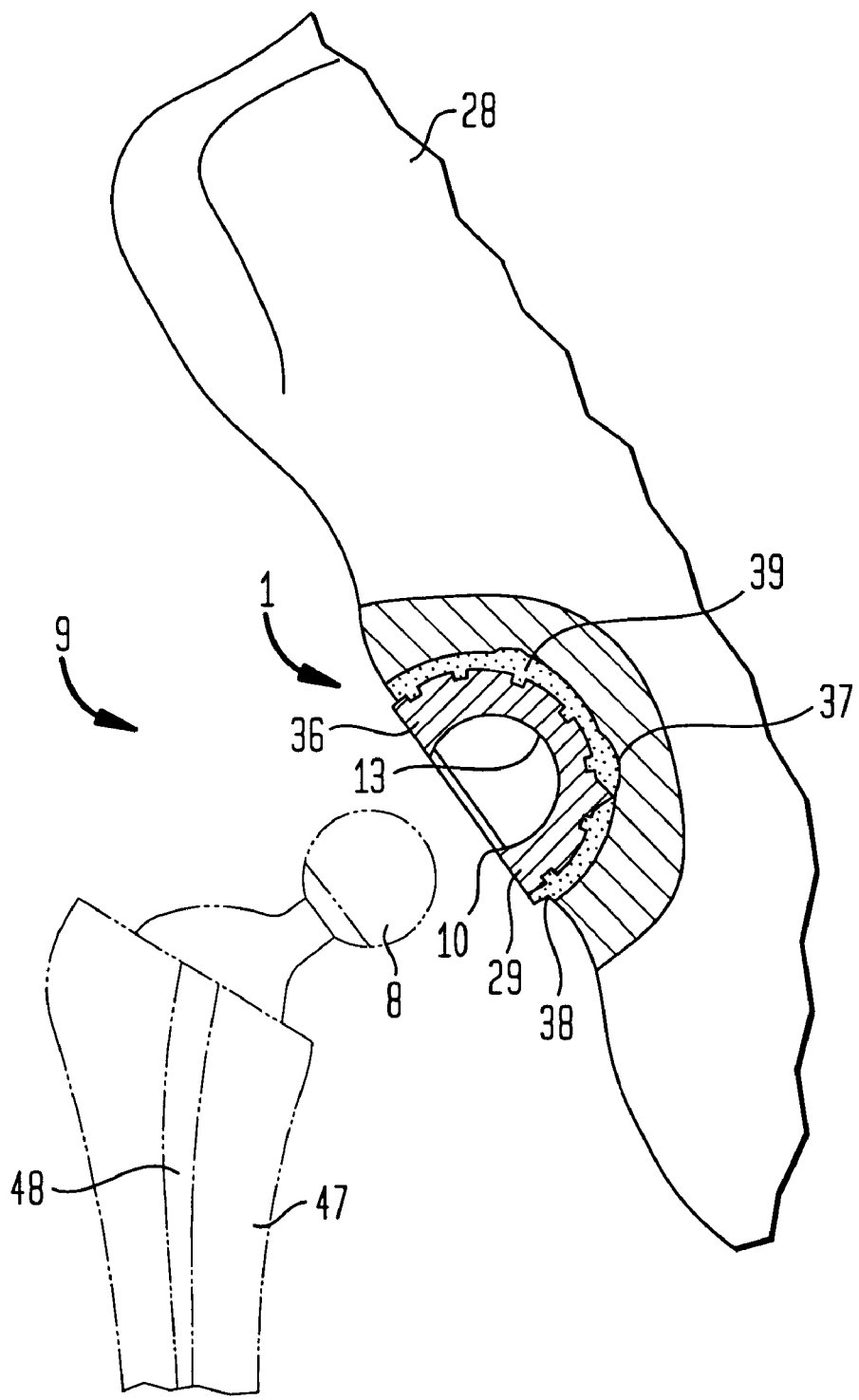
FIG. 1 is a schematic, partially sectional front view of an acetabular cup secured in a pelvic bone and a femur with a spherical head of an artificial hip joint.
Figure 4:
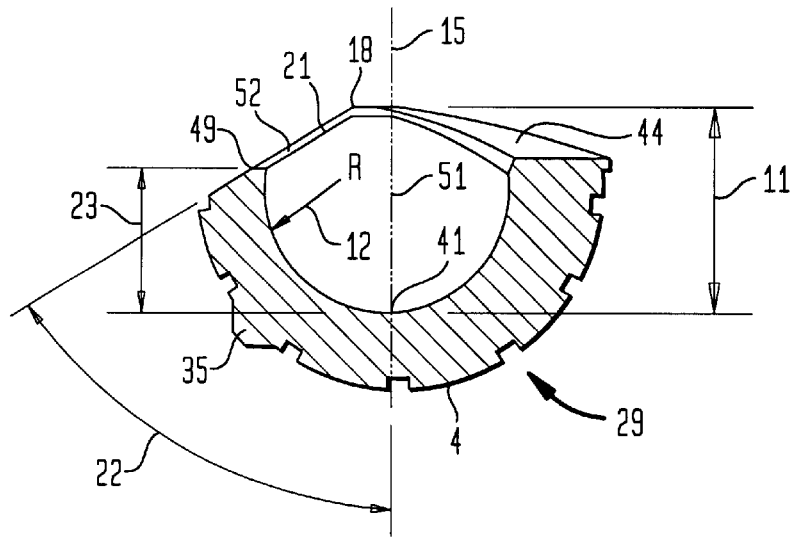
FIG. 4 is a side sectional view of the acetabular cup of FIG. 2 along the line IV—IV.
Figure 5:
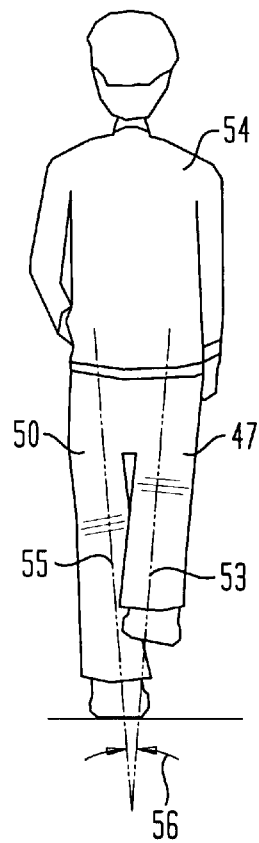
FIG. 5 is a rear view of a human with the right leg being slantingly angled rearwards.

An acetabular cup 1 includes essentially a bearing surface 2 with a receiving edge 3 and an outer surface 4 which is bounded by sectors 5, 6, 7. The receiving surface 2 is of concave configuration and may form a spherical section for receiving an articular head 8 which forms an artificial hip joint 9 with an acetabular cup 1. The articular head 8 may be formed as spherical head having secured thereto a stem 48 which can be anchored in a femur 47 extending, for example, through a right leg 53 of a human being 54.

The bearing surface 2 is bounded by the receiving edge 3. The bearing surface 2 includes an elevation 10 at the receiving edge 3 so that a spacing 11 is realized in this region between an apex 18, demarcating the elevation 10, and a lowest point 41 of the bearing surface, with the spacing being greater than a radius 12 of a spherical section 13 formed by the bearing surface 2.

The receiving edge 3 is configured in a first segment 14 as an edge which extends roughly in a horizontal plane 43. Extending substantially perpendicular upon this horizontal plane 43 is a cup axis 15 which runs through the bearing surface 2. The horizontal plane 43 bounds a spherical section formed by the bearing surface 2.

The first segment 14 of the receiving edge 3 terminates in a second segment 16 which includes the elevation 10 and ascends from a junction end 17, adjacent to the first segment 14, to an apex 18 or an apex line 40 of the elevation 10. A second sector angle 19 is defined by the second segment 16 between its junction end 17 and the apex 18. The second sector angle 19 is about 110°. The first segment 14 has a first end which is distal to the junction end 17 of the second segment 14, with a third segment 21 being arranged between the first end 20 of the first segment 14 and the apex 18 or the apex line 40 of the elevation 10 of the second segment 16. The third segment 21 includes an edge which is cut in a slanted plane 49. This slanted plane 49 extends at an acute angle 22 with respect to a plane 51 which extends perpendicular through the cup axis 15. The third segment 21 forms a pivot space 46 in which the stem 48, anchored in the femur 47, of the articular head 8 can execute swivel motions, for example, when a human being 54 walks.

For that reason, the edge slanted in the region of the third segment 7 is drawn fairly far into the bearing surface so that the bearing surface 2 has a reduced depth 23 in the region of the pivot space 46 with respect to the spacing 11 between the apex 18 and the lowest point 41. This depth 23 is smaller than a radius 12 of the spherical section 13. The third segment 21 defines a third sector angle 24 of about 115° between the first segment 14 and the second segment 16.

The elevation 10 has a sliding surface 42 which confronts the articular head 8 inserted in the bearing surface 2 and constitutes a part of the bearing surface forming surface of a spherical section. This sliding surface acts upon the articular head 8 inserted in the bearing surface 2.

The receiving edge 3 forms an inner boundary of a boundary surface composed of sectors 5, 6, 7, with the first segment 14 forming the inner boundary of the first sector 5, the second segment 16 forming the inner boundary of the second sector 6, and the third segment 21 forming the inner boundary of the third sector 7.

The second sector 6 is widened with respect to the first sector 5. By widening the second sector 6, a protrusion 27 is formed at the bottom side 26, facing away from the second sector 6, of the elevation 10 for support of the acetabular cup 1 upon the surrounding pelvic bone 28. The second segment 6 extends thereby in the form of an ascent 44 in the direction of the apex line 40 formed by the apex 18. The ascent 44 is defined by an ascending angle 45 from a level which is predetermined by the first sector 5. The ascending angle 45 ranges between 2° and 7°.

In order to enable a placement of the articular head 8 in the bearing surface 2, the slanted edge has in the area of the third sector 7 a cut-off edge 52 via which the articular head 8 can be inserted in the bearing surface 2. The cut-off edge 52 permits a considerable elevation of the third sector 7 relative to the inserted articular head 8.

The acetabular cup 1 is configured as a single-piece articular body 29. It is, however, also possible in principle to form the articular body, for example, for cementless anchoring by two or more shells which fit together. The articular body 29 is bounded to the inside by the bearing surface 2 and to the outside by the outer surface 4 which is arranged at a distance to the bearing surface 2.

The outer surface 4 has also a shell-shaped configuration, in particular, spherical configuration. The outer surface 4 has three concentric annular grooves 30, 32, 32. Arranged transversely to the annular grooves 30, 31, 32 are seventeen longitudinal grooves 33 which converge in a point. The longitudinal grooves 33 and the annular grooves 30, 31, 32 thus define a number of ring-shaped neighboring surface segments 34 which facilitate the cementing of the acetabular cup 1 in the pelvic bone 28. Arranged on the surface segments 34 of a center ring on each second surface segment 34 are spacers 35 which maintain a distance between the acetabular cup 1 with its outer surface 4 with respect to the neighboring pelvic bone 28 and provide for an even thickness of the bone cement layer being used.

Upon insertion of the acetabular cup 1, the cavity 37 of the pelvic bone 28, receiving the articular cups, is milled to the desired size, and the articular cup is placed with bone cement 39 in the cavity 37. The alignment of the articular body 29 and the acetabular cup 1 is realized in such a manner that the third sector 7 is arranged in the direction of a stem jutting out of the bearing surface 2 and projecting into the femur 47. In this way, the third sector 7 forms the pivot space 46 in which the stem 48 can execute swivel motions. In this alignment of the acetabular cup 1, the elevation 10 points in one direction in which, for example, the right leg 53, supported in the acetabular cup 1, of a human being 54 points slantingly rearwards and intersects at an acute angle an imaginary movement plane 55 defined by a standing leg 50 in a straight alignment.

What is claimed is:

1. An acetabular cup, comprising an outer surface, and a bearing surface (2), defining a sperical inner surface, for receiving an articular head (8) of an artificial hip joint, wherein the bearing surface (2) is bounded in surrounding relation by a receiving edge (3) and includes an elevation (10) which ascends from the receiving edge (3) to an apex (18) positioned at a distance to a lowest point (41) of the bearing surface 2, wherein the distance exceeds a radius (12) of the spherical inner surface, wherein the receiving edge (3) descends in the direction to the lowest point (41) such that the distance is less than the radius of the inner spherical surface thereby allowing for allowing a pivot space (46) for swingably supporting a stem (48) secured to the articular head (8).

2. The acetabular cup of claim 1, wherein the elevation (10) is provided at a location coinciding with the optimum freedom of movement of the articular head (8) when the head is received within the cup.

3. The acetabular cup of claim 1, wherein the elevation (10) is defined by a dimension extending from the apex projecting furthest from the receiving edge (3), and a distance from the apex (18) to the lowest point (41) of the bearing surface (2) which contains the articular head (B) in substantially surrounding relation.

4. The acetabular cup of claim 3, wherein the elevation (10) extends from the lowest point (41) of the bearing surface (2) to the apex (18) in a direction in which a femur (47) which receives the artificial hip joint (9) extends slantingly backwards with respect to a stretched standing leg (50) and thereby intersects at an acute angle (56) an imaginary movement plane (55) defined by the standing leg in straight alignment.

5. The acetabular cup of claim 3, wherein the receiving edge (3) is formed in a first segment (14) as an edge of a spherical section extending approximately in a horizontal plane (43) with a cup axis (15) oriented perpendicular thereto and extending through a lowest point (41).

6. The acetabular cup of claim 5, wherein the first segment (14) of the receiving edge terminates in a second segment (16) including the elevation (10) and which ascends from a junction end (17), where the second segment (16) borders on the first segment (14) to the apex (18) of the elevation (10).

7. The acetabular cup of claim 6, wherein the second segment (16) defines a sector angle (19) of about from 45° to 135°.

8. The acetabular cup of claim 7, wherein the second sector angle (19) is about 110°.

9. The acetabular cup of claim 6, wherein the second segment (16) of the receiving edge ascends at a constant angle with respect to a horizontal plane in the direction of the apex (18).

10. The acetabular cup of claim 10, wherein the ascent (44) has an ascending angle (45) of about 2° to 7°.

11. The acetabular cup of claim 5, wherein a third segment (21) located between the first section and the second section has the receiving edge (3) which descends in the direction to the lowest point (41) thereby defining the pivot space (46).

12. The acetabular cup of claim 11, wherein the pivot space (46) descends in the direction towards a first end (20) from the apex (18), and the receiving edge (3) is slanted in the area of the pivot space (46) in a plane (49) which extends at an acute angle (50) with respect to a plane (51) extending perpendicular through the cup axis (15).

13. The acetabular cup of claim 12 wherein the acute angle (5) ranges between 30° and 60°.

14. The acetabular cup of claim 12, wherein the acute angle (5) is 40°.

15. The acetabular cup of claim 12, wherein the receiving edge (3) in the pivot space (46) has a depth sufficient to guide the spherical head in form-fitting manner, and a cut-off edge (52) permitting the insertion of the spherical head in the bearing surface (2).

16. The acetabular cup of claim 12, wherein the third segment (21) defines between the first segment (14) and the second segment (16) in relation to the cup axis (15) a third sector angle (24) between about 90° and about 180°.

17. The acetabular cup of claim 16, wherein the third segment (21) defines a third sector angle (24) of about 115°.

18. The acetabular cup of claim 17, wherein the receiving edge (3) forms an inner, cup axis confronting, boundary of a surface composed of sectors (5, 6, 7).

19. The acetabular cup of claim 18, wherein the first segment (14) of the receiving edge (3) forms the inner boundary of the first sector (5), the second segment (16) forms the inner boundary of the second sector (6), and the third segment (21) forms the inner boundary of the third sector (7).

20. The acetabular cup of claim 18, wherein the second sector (6) is dimensioned wider than the first sector (5).

21. The acetabular cup of claim 1, configured as a unitary articular body (29).

22. The acetabular cup of claim 1, configured as a multi-part articular body (29).

23. The acetabular cup of claim 1, wherein the outer surface (4) has a substantially spherical configuration.

24. The acetabular cup of claim 23, wherein the outer surface (4) has a plurality of annular grooves (30, 31, 32) in substantial concentric relation to the cup axis (15).

25. The acetabular cup of claim 24, wherein the outer surface (4) has three concentric annular grooves (30, 31, 32).

26. The acetabular cup of claim 24, wherein the outer surface (4) has a plurality of longitudinal grooves (33) extending transversely to the annular grooves (30, 31, 32).

27. The acetabular cup of claim 26, wherein the outer surface (4) has about 17 longitudinal grooves (33).

28. The acetabular cup of claim 1, wherein the outer surface (4) has a plurality of spacers (35) in concentric relation to the cup axis (15).

29. The acetabular cup of claim 21, wherein the articular body (29) is made of plastic.

30. The acetabular cup of claim 29, wherein the articular body (29) is made of polyethylene.

31. The acetabular cup of claim 22, wherein the articular body (29) is made of plastic.

32. The acetabular cup of claim 31, wherein the articular body (29) is made of polyethylene.

* * * * *